United States Patent [19]

McCapra et al.

[11] Patent Number: 5,281,712
[45] Date of Patent: Jan. 25, 1994

[54] AMMONIUM SUBSTITUTED CHEMILUMINESCENT LABELS AND THEIR CONJUGATES, AND ASSAYS THEREFROM

[75] Inventors: Frank McCapra, Seaford, Great Britain; Beheshti Iraj, Edina; Kastooriranganathan Ramakrishnan, Eden Prairie, both of Minn.

[73] Assignee: London Diagnostics, Inc., Eden Prairie, Minn.

[21] Appl. No.: 859,994

[22] Filed: Mar. 30, 1992

Related U.S. Application Data

[63] Continuation-in-part of Ser. No. 140,040, Dec. 31, 1987, abandoned, and a continuation-in-part of Ser. No. 291,843, Dec. 29, 1988, abandoned, and a continuation-in-part of Ser. No. 418,956, Oct. 10, 1989, abandoned.

[51] Int. Cl.$^5$ .............................................. C07D 219/04
[52] U.S. Cl. .................................... 546/104; 436/501; 530/409; 544/355; 546/61; 546/71; 546/93; 546/102; 546/107; 546/108; 546/112; 546/147; 546/170; 548/309.4
[58] Field of Search ............... 546/79, 93, 102, 104, 546/107, 108, 61, 112, 147, 170; 436/501; 530/409; 544/355; 548/309.4

[56] References Cited

U.S. PATENT DOCUMENTS

| | | | |
|---|---|---|---|
| 3,352,791 | 11/1967 | Sheehan et al. | 546/102 X |
| 3,689,391 | 9/1972 | Ullman | 546/102 X |
| 4,745,181 | 5/1988 | Law et al. | 546/104 X |
| 4,918,192 | 4/1990 | Law et al. | 546/104 |
| 4,946,958 | 8/1990 | Campbell et al. | 546/104 |
| 4,950,613 | 8/1990 | Arnold et al. | 546/104 |
| 5,110,932 | 5/1992 | Law et al. | 546/102 |

FOREIGN PATENT DOCUMENTS

| | | | |
|---|---|---|---|
| 216553 | 4/1987 | European Pat. Off. | 546/102 |
| 324202 | 7/1989 | European Pat. Off. | 546/102 |
| 330050 | 8/1989 | European Pat. Off. | 546/104 |
| 361817 | 4/1990 | European Pat. Off. | 546/102 |
| 1461877 | 1/1977 | United Kingdom | 546/102 |

*Primary Examiner*—Richard L. Raymond
*Attorney, Agent, or Firm*—George A. Skoler

[57] ABSTRACT

A novel chemiluminescent labeling compositions comprising an ester or thiolester covalently and jointly bonded to (1) a carbon of a heterocyclic ring or ring system that is susceptible to attack by peroxide or molecular oxygen and (2) an aryl ring or ring system wherein the heterocyclic ring or ring system is distinquished by a heteroatom thereof in an oxidation state which causes the attacked carbon atom to form an intermediate that decays and produces chemiluminescence; the aryl ring or ring system contains at least three substituents on a six-member aromatic hydrocarbon that together sterically and electronically hinder hydrolysis of the linkage, which substituents involve ortho substituent groups on the aryl in conjunction with quaternary ammonium meta or para substituents thereon. Included are the chemiluminescent labeling composition conjugated with a specific binding material; a chemiluminescent assay comprising the conjugate; and a chemiluminescent assay kit comprising the conjugate with the capability of conducting the assay.

18 Claims, No Drawings

AMMONIUM SUBSTITUTED CHEMILUMINESCENT LABELS AND THEIR CONJUGATES, AND ASSAYS THEREFROM

RELATED APPLICATIONS

This application is a continuation-in-part of application Ser. No. 140,040, filed Dec. 31, 1987, now abandoned, copending application Ser. No. 291,843, filed Dec. 29, 1988, now abandoned, and copending application Ser. No. 418,956, filed Oct. 10, 1989, now abandoned.

BRIEF DESCRIPTION OF THE INVENTION

This invention relates to unique chemiluminescent labeling compounds, conjugates containing associated versions of the labeling compounds, assays and kits for performing such assay utilizing the conjugates. The labeling compounds contain special sterically-hindered aryl heterocyclic esters and thiolesters by virtue of the presence of a quaternary ammonium substituent directly attached to the aryl group.

BACKGROUND TO THE INVENTION

The literature describes classes of compounds that give off light or "luminesce" by reaction through chemical treatment. The compounds that have this capability are termed chemiluminescent materials. Their dissociation is typically caused by treatment with peroxide or molecular oxygen at high pH. Light is produced by the decay of the transient ("intermediate") structure formed by peroxide or molecular oxygen reaction at an $sp^2$ or $sp^3$ hybridized carbon in the compound that is part of a chain or a ring or ring system.

As the literature indicates, any series of reactions which produce the intermediate:

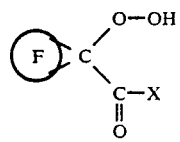

will lead to moderate to strong chemiluminescence. Ⓕ is a structure such that the product carbonyl derivative

is fluorescent and X is a good leaving group, usually with XH, for efficient chemiluminescence, having a $pK_a$ of about $\leq 11$, preferably $<11$, and most preferably, from about 5 to about 8. The reaction may require base catalysis. The intermediate can be prepared (in isolable or transient form, depending on Ⓕ) from species such as:

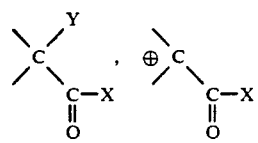

and $H_2O_2$(Y is halogen, $-OSO_2R$, and the like) or base/$O_2$. See *Endeavour*, 23, No. 117 (1973) p. 140, *The Chemistry of Bioluminescence* in "*Bioluminescence in Action*" (P. J. Herring, ed.), Academic Press, London, 1978 (pp. 64-5), *Proc. R. Soc. Lond.*, B 215, p. 256 (1982), *Progress in Organic Chemistry*, (W. Carruthers and J. K. Sutherland, eds.), Butterworth, London (1973), p. 261, all authored by F. McCapra.

For example, chemiluminescent aryl esters that contain such hybridized carbon, termed a labeling compound, react according to the following general reaction:

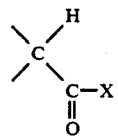

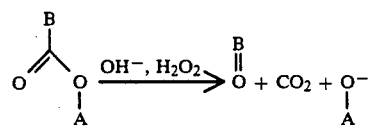

where A is an aryl ring or ring system and B is a heterocyclic ring or ring system. In this reaction, —O—A, the leaving group, is cleaved by perhydrolysis resulting in steps leading to the transient intermediate, B=O, that proceeds to decay generating luminescence.

The characteristics of some of these chemiluminescent compounds, their chemistry of manufacture, and other factors relating to them, are more fully described by McCapra, "Chemiluminescence of Organic Compounds," in Progress in Organic Chemistry, vol. 8, Carruthers and Sutherland ed., Wiley & Sons (1973); Kohen, Bayer, Wilechek, Barnard, Kim, Colleins, Beheshti, Richardson and McCapra, "Development Of Luminescence-Based Immunoassays For Haptens And For Peptide Hormones," pp. 149-158, in *Analytical Applications Of Bioluminescence and Chemiluminescence*, Academic Press, Inc. (1984); Richardson, Kim, Barnard, Collins and McCapra, *Clinical Chemistry*, vol. 31, no. 10, pp. 1664-1668 (1985); McCapra, "The Application of Chemiluminescence in Diagnostics," 40th Conference of the American Association of Clinical Chemists, New Orleans, La., Jul. 28, 1988; McCapra, "The Chemiluminescence Of Organic Compounds," Quarterly Reviews, vol. 20, pp. 485-510 (1966); McCapra, "The Chemiluminescence Of Organic Compounds," *Pure and Applied Chemistry*, vol. 24, pp. 611-629 (1970); McCapra, "The chemistry of bioluminescence," *Proceedings Of Royal Society*, vol. B215, pp. 247-278 (1982); McCapra and Beheshti, "Selected Chemical Reactions That Produce Light," *Bioluminescence and Chemiluminescence: Instruments and Applications*, CRC Press, vol. 1, Chapter 2, pp. 9-37 (1985); McCapra, "Chemiluminescent Reactions of Acridines," Chapt. IX, *Acridines*, R. M. Acheson, Ed., pp. 615-630, John Wiley & Sons, Inc. (1973); McCapra, "Chemical Mechanisms in Bioluminescence," *Accounts Of Chemical Research*, vol. 9, no. 6, pp. 201-208 (June 1976); and in many other publications and presentations on the subject.

As noted in the above literature, chemiluminescent compounds of a variety of structures have been projected as labels for a variety of assays including immunoassays (in this respect, see U.S. Pat. Nos. 4,383,031, 4,380,580 and 4,226,993). The esters and thiolesters, alone or conjugated (i.e., chemically coupled to another material), are especially desirable forms of chemiluminescent labels. However, they lose their luminescence capability over time in an aqueous system because they hydrolyze to products that are not available to the assay. Until recently, these compounds have not been used in commercial assays. Until this invention, the ester, thiolester and amide forms of this class of materials lacked sufficient hydrolytic stability to be stored in the most convenient form over an extended period of time, which is as a component of an aqueous system.

It is well understood in chemistry that carboxylic acid esters and thiolesters are susceptable to hydrolytic attack resulting in the formation of the carboxylic acid and the hydroxy, mercapto or amino component that is the theoretical or actual precursor to the ester, thiolester or amide. Hydrolysis is more pronounced under acid or basic conditions. It is also recognized in chemistry that certain levels of hydrolysis can be inhibited by the inclusion of properly positioned bulky groups that chemically sterically hinder those linkages, see Nishioka et al., *J. Org. Chem.*, vol. 40, no. 17, pp. 2520–2525 (1975), Fujita et al., "The Analysis of the Ortho Effect," *Progress in Physical Organic Chemistry*, 8, pp. 49–89 (1976), Morrison and Boyd, *Organic Chemistry*, 5th Ed., pp. 842–843 (1987) and March, *Advanced Organic Chemistry*, 3rd Ed., page 240 (1985). According to March:

"Another example of steric hindrance is found in 2,6-disubstituted benzoic acids, which are difficult to esterify no matter what the resonance or field effects of the groups in the 2 or the 6 position. Similarly, once the 2,6-disubstituted benzoic acids *are* esterified, the esters are difficult to hydrolyze."

The difficulty in esterification is not the same in making esters from 2,6-substituted phenols, but the general principles described by March are applicable to enhancing the hydrolytic stability of the resultant ester so long as the ortho substitutions are electron donating. As this invention demonstrates, effective levels of hydrolytic stability require the presence of a select level of electron withdrawing chemical effect in conjunction with (and in addition to) traditional chemical steric hindrance factors.

The functional electron withdrawing or electron donating characteristics of a group in an organic compound is conventionally measured relative to hydrogen. This relative ranking accepts that all groups on a molecule will provide some electron withdrawing effect, and distinguishes them by the nature of impact the group has on the molecule's performance. An electron withdrawing functional group, characterized by a positive number, will draw electrons to itself more than hydrogen would if it occupied the same position in the molecule. The opposite occurs with an "electron donating group," a lesser electron withdrawing group which chemical convention characterizes by a negative number. Sigma para values ($\sigma_p$) are the relative measurement of electron withdrawing or electron donating qualities of a functional group in the para position on benzoic acid. See March, *Advanced Organic Chemistry*, 3rd Edition, Publ. by John Wiley & Sons, New York, N.Y. (1985) at pp. 242–250 and 617–8. Tables of $\sigma_p$ values for various groups can be found in Hansch et al., *J. Med. Chem.* 16(11): 1209–1213 (1973) and Hansch and Leo, "Substituent Constants for Correlation Analysis in Chemistry and Biology," Ch. 6, pp. 49–52 (John Wiley & Sons, New York 1979). The $\sigma_p$ values reported in the Hansch articles are relied on herein in characterizing relative values for groups both in the meta and para position.

The function of chemiluminescent labels in assay applications involves the coupling of the label compound to a substrate molecule. Such coupling can be achieved by solvent interraction (e.g., molecular compatibility), any heterolytic or homolytic mechanism induced by chemical means and influenced by physical effects, such as time, temperature and/or mass action. For example, the reaction can be nucleophilic or electrophilic, or it can involve free radical mechanisms. In the broadest perspective, the coupling can be viewed as achievable via strong to weak bonding forces.

A chemiluminescent label in assays is an associated moiety of a binding material. The moiety is derived from a chemical compound which, as such, possesses chemiluminescent capabilities. Hereinafter, the term moiety as applied to the label as such, is a reference to the compound prior to being associated with a binding material. The term associated is intended to include all or any of the mechanisms for coupling the label to the substrate molecule.

The term "functional" in chemistry typically refers to a group that influences the performance of a chemical or constitutes the site for homolytic or heterolytic reactions. For example, a functional alkyl substituent, used in the context of interreactions through that substituent, means an alkyl group substituted so that it can effect that reaction. But an alkyl group termed functional for the electronic effects it induces in the molecule is a reference to the alkyl group per se.

THE INVENTION

This invention relates to unique quaternary ammonium containing chemiluminescent labeling compounds, conjugates containing associated versions of the labeling compounds, assays and kits for performing such assay utilizing the conjugates. The labeling compounds contain special sterically-hindered aryl heterocyclic substituted esters and thiolesters that contain quaternary ammonium groups directly bound to the aryl moiety.

This invention relates to novel chemiluminescent labeling compositions and their conjugates with specific binding materials that are normally maintained in an aqueous medium. These compositions and the conjugates find special application in specific binding assays because the chemiluminescent compound, i.e., the labeled moiety, has increased and unique stability in aqueous mediums and exceptional chemiluminescence qualities.

The novel root compound of the invention is a chemiluminescent compound characterized by the presence an aryl ester, thiolester or amide of a carboxylic acid substituted heterocyclic ring that is susceptible to chemical attack (such as by oxidic attack) of the heterocyclic form a transient compound in the manner characterized above. The heterocyclic ring is ring carbon-bonded to the carbonyl of the ester, thiolester and amide moiety and possesses a heteroatom in an oxidation state that allows chemiluminescence by dissociating a compound at the carbon bonded to the carbonyl ("intermediate") that decays to produce chemiluminescence. The aryl ring or ring system is ring carbon-bonded to the oxygen or sulfur of the ester or thiolester, as the case may be, and contains at least three substituents on a six-member ring. The substitution on the six-member ring comprises three or more groups acting in concert to sterically and electronically hinder hydrolysis of the ester, thiolester or amide linkage. Significant to this invention is the presence of diortho electron donating substitutions on the aryl unit in conjunction with a meta or para positioned quaternary ammonium substituent. It is this combination that causes the chemiluminescent label compound to have uniquely high hydrolytic stability.

Also in accordance with the present invention are conjugates of the labeling composition, assay systems utilizing the conjugates, and assay kits incorporating such chemiluminescent labels.

In particular, this invention relates to a hydrolytically stable heterocyclic composition capable of chemiluminescent properties when labeled (i.e., affixed as a label) to a specific binding material by chemically-induced dissociation, comprising (a) an aryl ring,
(b) a sterically-hindered ester, thiolester or amide linkage moiety with enhanced hydrolytic stability, and
(c) a heterocyclic organic ring moiety, in which
   (1) the carbonyl carbon of (b) is covalently bonded to a carbon atom (x) of (c) and the remaining free valence of (b) is carbon bonded to an aromatic ring carbon atom (y) of (a),
   (2) (a) contains at least three substituent groups hindering hydrolysis of (b), two of which are electron donating and located on the ring carbon atoms adjacent to (y), the remainder is a quaternary ammonium that is meta or para to (y), and
   (3) (c) contains
      (i) at least one ring carbon atom adjacent to said ring carbon atom (x), and
      (ii) a ring member heteroatom in an oxidation state that provides such chemiluminescence properties.

Also, this invention contemplates hydrolytically stable conjugates possessing chemiluminescent properties by chemical dissociation, comprising a chemiluminescent label bonded to a specific binding material that contains (a) an aryl ring,
(b) a sterically-hindered ester or thiolester linkage moiety with enhanced hydrolytic stability, and
(c) a heterocyclic organic ring moiety, in which
   (1) the carbonyl carbon of (b) is covalently bonded to a carbon atom (x) of (c) and the remaining free valence of (b) is carbon bonded to an aromatic ring carbon atom (y) of (a),
   (2) (a) contains at least three substituent groups hindering hydrolysis of (b), two of which are electron donating and located on the ring carbon atoms adjacent to (y), the remainder is quaternary ammonium that is meta or para to (y), and
   (3) (c) contains
      (i) at least one ring carbon atom adjacent to said ring carbon atom (x), and
      (ii) a ring member heteroatom that is in an oxidation state whereby reaction of molecular oxygen or a peroxide with said composition forms an intermediate which decays to produce chemiluminescence.

The invention encompasses a method for assaying the presence of an analyte in a sample. The method comprises contacting an analyte with the aforementioned chemiluminescent-labeled specific binding material (the "conjugate"), inducing chemiluminescence by decay of an intermediate dissociated from the conjugate, and measuring luminescence therefrom to assay the analyte.

In keeping with the inventive chemiluminescent-label's function of assaying, the invention embodies a specific binding assay kit comprising a vial containing a conjugate possessing chemiluminescent properties by chemically induced dissociation and containing the aforementioned chemiluminescent label bonded to a specific binding material.

The invention recognizes that hydrolytic stability of a chemiluminescent label composition that utilizes aryl ester, thiolesters, and amides, as defined herein, linked to heterocyclic carboxy compounds, is affected by two factors. The first is the utilization of diortho substitution on the aryl ring of a kind that traditionally contributes to hydrolytic stability. This is the "bulky group" steric hindrance effect noted by Morrison and Boyd, supra. In the context of sigma values, these bulky groups are typically classed as electron donating. The second is the utilization of meta and/or para substitution on the same ring that untraditionally contributes to hydrolytic stability. This latter substitution is a quaternary ammonium, such as $-N(CH_3)_3^+$, group directly bonded to the ring. This combination of steric hindrance and the quaternary ammonium group provides materially superior hydrolytic stability to the labeling composition than most other substituents.

DETAILED DESCRIPTION OF THE INVENTION

As mentioned above, proper positioning of bulky groups in an ester enhances the ester's hydrolytic stability. In the case of an aryl ester, steric hindrance is expected with bulky groups that block the ester moiety. Those groups may be provided on the aryl group in the ortho positions relative to the juncture with the ester moiety. Groups that may be dormant to any other reaction may not provide steric hindrance because of its chemical nature. For example, a group in a position alpha to a carbonyl moiety of an ester group that is electron withdrawing (such as an alpha chloro group) could adversely affect the hydrolytic stability of the ester group. However, a methyl electron donating group in the same position enhances hydrolytic stability. Thus, the relative position of the bulky group and its chemical nature is important to steric hindrance. As a result, the typical bulky group provided in the ortho position of an aryl ester for steric hindrance is electron donating. An electron withdrawing group would be expected to adversely affect the hydrolytic stability of the aryl ester. The presence of an electron withdrawing group substituted on an aryl ester would be expected to, to some degree, as a result of the field effects they introduce, reduce the hydrolytic stability of the ester, even if it is otherwise substituted with electron donating groups in the ortho positions. The presence of the electron withdrawing group would be expected to reduce the electron flow provided by the ortho electron donating groups to the ester group. It has been determined that the presence of meta or para positioned quaternary ammonium groups, such as $-N(CH_3)_3^+$, enhances the hydrolytic stability of the ester group over that achievable by the use of the conventional bulky groups even located in the ortho positions.

The chemiluminescent compounds of the present invention have the following schematic formula:

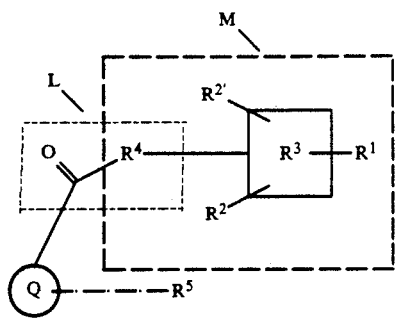

I.

In schematic formula 1., the hatched-line box labeled "L" contains the ester or thiolester "linkage" which is carbon-bonded between two substituted rings or ring systems represented by the circle labeled "Q" and the solid box labeled "$R^3$". Whether the linkage L is an ester or thiolester is determined by $R^4$ being —O— or —S—, respectively. The preferred linkage is the ester. M encompasses the leaving group comprising a portion of L and moiety $R^3$ with its associated $R^1$, $R^2$ and $R^{2'}$. M would be the leaving group even if $R^1$ were conjugated to a specific binding material. The leaving group possesses the typical $pK_a$ of about $\leq 11$.

Q is a heterocyclic ring or ring system to which the ester or thiolester linkage L is attached at a carbon atom within the heterocyclic ring or ring system. That carbon atom (1) is either $sp^2$ or $sp^3$ hybridized, and (2) is susceptible to attack by peroxide or molecular oxygen to form the intermediate that decays to produce chemiluminescence. The oxidation state of the heteroatom within the heterocyclic ring or ring system will determine whether the carbon atom is susceptible to such attack. If the carbon to which the linkage is attached is $sp^2$ hybridized, the heteroatom is in a positive oxidation state (i.e., have a positive charge, for example, as obtained by N-alkylation or N-oxidation). If the carbon to which the linkage is attached is $sp^3$ hybridized, the heteroatom is in a neutral oxidation state (i.e., uncharged). When the heteroatom is nitrogen, proper oxidation states can be achieved only if the nitrogen is substituted with an alkyl group (including a reactive functionalized alkyl group), an aryl group (including a reactive functionalized aryl group), —O— (if the nitrogen is in a positive oxidation state) or —OH (if the nitrogen is in a neutral oxidation state). When the heteroatom is in these "proper" oxidation states, the carbon atom will be susceptible to attack by peroxide or molecular oxygen to produce the chemiluminescent intermediate.

Heterocyclic rings or ring systems that contain the heteroatom in a positive oxidation state include without limitation acridinium, benz[a]acridinium, benz[b]acridinium, benz[c]acridinium, a 1,2,4-triazole cation, an isooxazole cation, an isothioazole cation, a 1,2-azole cation, an imidazole cation, a benzimidazole cation, quinolinium, isoquinolinium, quinolizinium, a cyclic substituted quinolinium, pyridinium, pyrimidininium, pyridazinium, pyrazininium, phenanthridinium, and quinoxalinium. Rings or ring systems in which the heteroatom is in a neutral oxidation state include the reduced forms of the foregoing. These rings or ring systems are derived from the following rings or ring systems:

Acridine Series

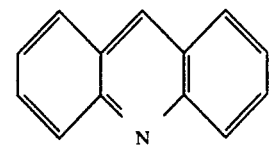
Acridine

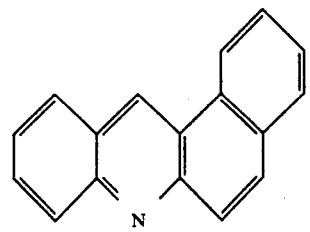
Benz[a]acridine

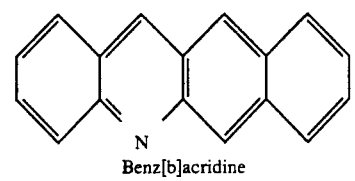
Benz[b]acridine

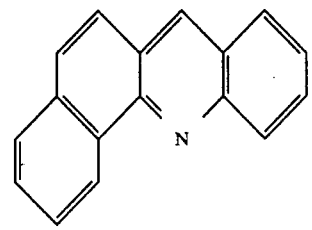
Benz[c]acridine

Azole Series

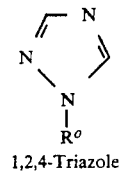
1,2,4-Triazole

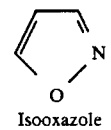
Isooxazole

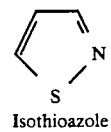
Isothioazole

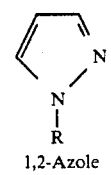
1,2-Azole

-continued

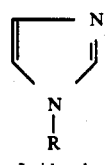
Imidazole

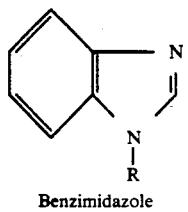
Benzimidazole

Quinoline Series

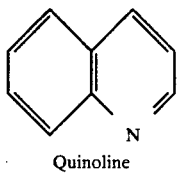
Quinoline

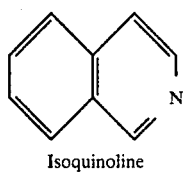
Isoquinoline

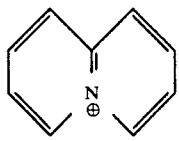
Quinolixinium Cations

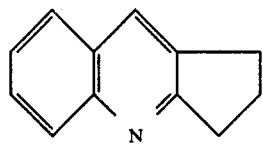

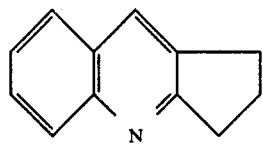

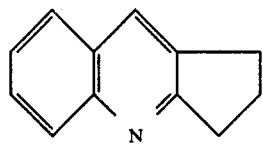
Cyclic C3, C4, C5-Substituted Quinolines

Pyridine/Pyrimidine Series

-continued

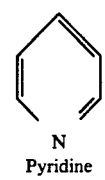
Pyridine

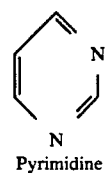
Pyrimidine

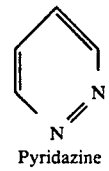
Pyridazine

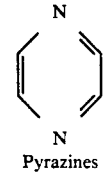
Pyrazines

Miscellaneous

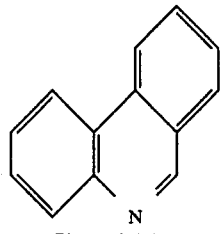
Phenanthridine

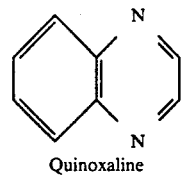
Quinoxaline

The aryl ring or ring system, represented by $R^3$, includes at least one substituted six-member ring of the formula

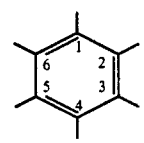

in which the substituents comprise at least a quaternary ammonium group, such as

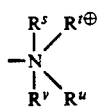

wherein $R^s$, $R^t$, $R^u$ and $R^v$ are individually alkyl ($C_{1-18}$), aryl (such as phenyl, anthracyl, and the like), alkaryl (methyl phenyl, and the like), aralkyl (benzyl, phenylethyl, and the like), or cycloalkyl ($C_{5-8}$, and the like), organofunctional groups bonded to alkyl ($C_{1-8}$) or aryl, wherein the organofunctionality includes the functional groups described below bonded to the quaternary ammonium nitrogen through such alkyl or aryl moieties. A preferred quaternary ammonium group is $-N(CH_3)_3^+$. The quaternary ammonium groups are positioned at ring carbons 3, 4 or 5, and $R^2$ and $R^{2'}$ at ring carbons 2 and 6. The ester or thiolester linkage is directly attached through a covalent bond to such six-member ring at ring carbon 1. $R^3$ may include but is not limited to phenyl, naphthyl and anthracyl, which are derivatives of the following structures:

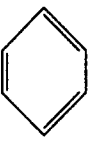

Phenylene

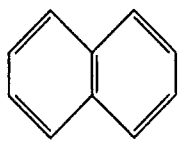

Naphthalene

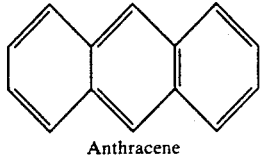

Anthracene

In those cases where naphthyl or anthracyl rings are employed, one of the rings constitutes $R^3$ and the other ring or rings in combination with it are formed via ring carbons thereof other than carbon 1. $R^3$ linked through carbon 1 may be substituted at any aromatic carbon position provided carbon atoms 2 and 6 are appropriately substituted with electron donating groups and one or more of carbons 3, 4 and 5 are appropriately substituted with a group having a $\sigma_p$ value greater than 0 and less than 1.

$R^3$ may include, but is not limited to, quaternary ammonium and the substituent groups designated for $R^1$, $R^2$ and $R^{2'}$ described below. However, in the practice of the invention, the presence of the quaternary ammonium group is necessary. $R^3$ may be attached through substituents $R^1$ to protein or other material. In that case, where the attachment is via a nucleophilic substitution reaction, then the linkage unit attached to $R^3$ and the protein or other material, may in addition to quaternary ammonium (preferably via an organofunctional group therein), be another nucleophilically reactive group.

$R^2$ and $R^{2'}$ are the classic bulky electron donating groups which are located on $R^3$ at $C_2$ and $C_6$ so as to sterically hinder, in the traditional manner, the hydrolysis of the linkage L between $R^3$ and the heterocyclic ring or ring system Q. Where $R^3$ is phenyl with the ester linkage being attached at position 1, $R^2$ and $R^{2'}$ are located at the ortho 2 and 6 positions. $R^2$ and $R^{2'}$ may be the same or different, and either may include:

an alkyl ($C_{1-4}$) or optionally functionalized alkyl ($C_{1-4}$) group an aryl or optionally functionalized aryl group $-OR$, where R is alkyl ($C_{1-4}$) or aryl $-SR$, where R is alkyl ($C_{1-4}$) or aryl.

The required steric hindrance can also be provided by other rings within a multi-ring $R^3$ which are "adjacent" to the six-member ring to which the ester linkage is attached. For example, if $R^3$ is naphthyl and an ester linkage is attached at the 1 position, $R^2$ could be a methyl group at the 2 position and $R^{2'}$ is the "adjacent" ring containing carbons 7-10. In such cases, the adjacent ring is considered, in the classic sense of steric hindrance, to be an electron donating substituent (on the six-member ring within $R^3$) which sterically hinders the hydrolysis of the linkage.

$R^1$ in the preferred embodiment, provides a quaternary ammonium group such as $-N(CH_3)_3^+$ directly bonded to the aryl carbon atom in one of the meta or para position. It may also provide the capability of entering into a bonding relationship with an active hydrogen containing group such as amino, amido, carboxyl, hydroxyl, thiol, and the like. The bonding capability of $R^1$ need only be sufficient to link the label compound to the active hydrogen containing group. Such bonding may be covalent, ionic, hydrogen and other associative bonding that would be acceptable for linking with the composition containing the active hydrogen to which bonding is desired.

Particularly desirable $R^1$ groups, other than the $-N(CH_3)_3^+$ group, are those that are directly bonded to the $R^3$ ring $C_{3,4 \ and/or \ 5}$ atoms through a non-carbon and non-oxygen unit. The preferred $R^1$ groups contain non-carbon and non-oxygen radicals such as N, S, P, B, Si, and the like, bonded to one or more of the $C_{3,4 \ and/or \ 5}$ atoms or substituted alkoxy and alkyl. Each of these preferred groups frequently contain bonded to them one or more of oxo (i.e., $=O$), oxy (i.e., $-O-$), halogen, and carbon bonded organic moieties. When all of the free valences of the radicals are saturated with carbon bonded organic, then the group is an onium, such as quaternary ammonium, sulfonium, phosphonium, and the like. Desirable groups include the following:

$-NO_2$
$-SO_2-$halogen
$-Br$
$-N(CH_3)_3^+$
$-B(OH)_2$
$-CF_3$
$-SO_2CH_3$
$-OCF_3$

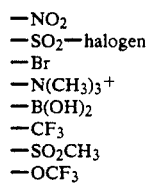

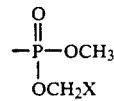

-continued

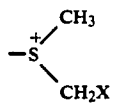

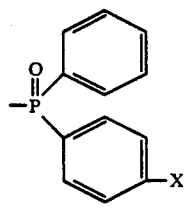

—C=NH$_2$, where R$^7$ is a residue of an alcohol
  |
  OR$^7$

—N=C=S

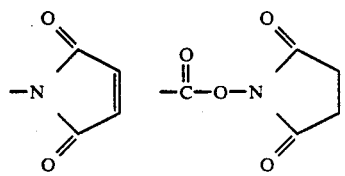

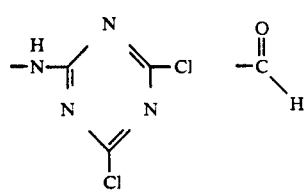

—N$_3$ and other photolabile functionalities in which halogen may be fluorine, chlorine, bromine and iodine, chlorine being the most preferred, X is a functional group reactive with active hydrogen, such as carboxyl halide, sulfonyl halide, and amino. The essential group with respect to this invention is the quaternary ammonium, such as —N(CH$_3$)$_3$$^+$. The SO$_2$Cl group provides exceptional bonding to proteins and extremely sensitive assay systems.

As noted above, the same functional groups may be part of the quaternary ammonium group. In that context, they are bonded to alkyl or aryl that in turn is bonded to the nitrogen of the quaternary ammonium group. Thus, such functional groups may be independent of the quaternary ammonium group or part of it. This allows a broad selection of useful functionality for the conjugation of the label to an analyte or specific binding material, as described below.

The heterocyclic ring or ring system may contain substitutions not shown in schematic formula I. When the heterocyclic ring or ring system contains substitution, the substitution may be at any position, including the heteroatom. Such rings and ring systems, whether or not substituted, are considered herein to be within the meaning of the term "heterocyclic ring or ring system."

Suitable ring substitutions R$^5$, may be functional or non-functional. Functionality can be for the purpose of enhancing the hydrolytic stability of the compound or for providing coupling capabilities via homolytic or heterolytic reactions or other forms of association that couple the label compound to its substrate. Such substitutions include those for the purposes of producing peri-interactions around the linkage L to enhance its hydrolytic stability, providing functionality to the compound for coupling to proteins and other materials with complementary functionality, and increasing the compound's solubility and chemiluminescent efficiency. Groups useful for associating the compound to proteins and other materials so that the chemiluminescent label compounds of the invention function in a coupled state with them include, but are not limited to, the following functionally substituted moieties as —CO$_2$R$^6$, where R$^6$ is hydrogen, alkyl or aryl —C=NH$_2$, where R$^7$ is a residue of an alcohol
  |
  OR$^7$ —SO$_2$Cl

—NCS

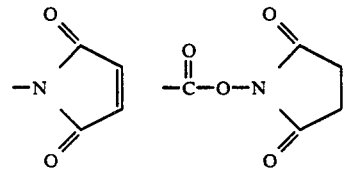

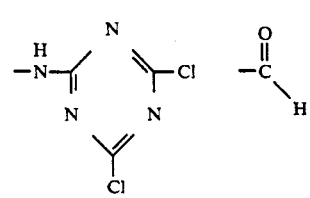

—N(CH$_3$)$_2$(CH$_2$)$_m$Cl, where m is equal to or greater than 1

—N$_3$ and other photolabile functionalities

—NH$_2$ or oniums (such as quaternary ammoniums, phosphoniums, sulfoniums, and the like), sugars, polyalkylenepolyamines and polyalkyleneoxide (e.g., polyoxyethylene, polyoxy-1,2-propylene, polyoxy-1,3-propylene, polyoxy-1,2-butylene, etc.), and the like. Other chains, groups and functionalities useful for attaching compounds of the present invention to protein are discussed in Ji, "Bifunctional Reagents," Meth. Enzymology 91:580 (1983), which is incorporated herein by reference. Methods of joining such attaching groups to protein and other materials utilize both covalent bonding and weaker chemical forces, and are well known in the art.

These functional groups may be bonded to the heterocyclic ring by a carbon to carbon bond, an oxygen to carbon bond, a nitrogen to carbon bond, and the like. It is desired that the hydrolytic stability of the bond to the heterocyclic ring be greater than that of the linkage achieved through reaction of the functional group and its complementary group on the substrate to which the label is being affixed.

Peri substituents, which can cause peri-interactions, include any group which can cause steric hindrance with respect to the carbon to which the ester, thiolester or amide linkage is attached and/or with respect to the carbon within the ester, thiolester of amide linkage. Preferred peri substituents include short alkyl groups (e.g., methyl, ethyl, and the like), aryl groups (e.g., phenyl), alkaryl (e.g., tolyl, xylyl, and the like), alkoxyalkyl (e.g., methoxymethyl, ethoxyethyl, and the like). The peri substituents, if present, are located on carbon atoms within the heterocyclic ring or ring system which are "adjacent to" the carbon to which the ester, thiolester or amide L linkage is attached. Moieties can include more than one peri substituent. For example, peri substituents can be placed in the following positions:

(a) in acridiniums and acridans: on $C_1$ and $C_8$;

(b) in phenanthridiniums and reduced phenanthridiniums: on $C_7$; and (c) in quinoliniums and reduced quinoliniums: on $C_3$.

As noted above, covalent or ionic attachment to proteins and other materials can be effected through substitutions on $R^3$ or Q's $R^5$.

The novel esters, thiolesters and amides of the invention are produced by conventional procedures in the art. For an example, a heterocyclic acyl halide of the formula

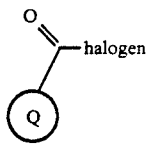

may be reacted with an aromatic 1-hydroxy or 1-mercapto containing the desired diortho (2,6) substitution, to form the desired L linkage. In some cases, the aromatic hydroxy or mercapto will contain, as well, the $R^1$ functionality. In other cases, it will be necessary to react the resultant esters, thiolesters and amides with reagents suitable for introducing the $R^1$ functionality.

In many cases, the reactions will proceed to the formation of intermediates that require separation for the next reaction step or final products that require isolation. In such cases, conventional techniques such as distillation, extraction, crystallization, washing and the like, will be required. Conventional separation by the addition of non-solvent to a solvent solution to force precipitation of a desired material is frequently found useful.

The above-described improved chemiluminescent compounds are useful in a broad range of specific binding assays for the presence of analyte in a sample. "Presence" shall mean herein the qualitative and/or quantitative detection of an analyte. Such assays may be directed at any analyte which may be detected by use of the improved chemiluminescent compound in conjunction with specific binding reactions to form a moiety thereon. These assays include, without limitation, immunoassays, protein binding assays and nucleic acid hybridization assays.

In a typical immunoassay, the analyte is immunoreactive and its presence in a sample may be determined by virtue of its immunoreaction with an assay reagent. In a typical protein binding assay, the presence of analyte in a sample is determined by the specific binding reactivity of the analyte with an assay reagent where the reactivity is other than immunoreactivity. Examples of this include enzyme-substrate recognition and the binding affinity of avidin for biotin. In the typical nucleic acid hybridization assay, the presence of analyte in a sample is determined by a hybridization reaction of the analyte with an assay reagent. Analyte nucleic acid (usually present as double stranded DNA or RNA) is usually first converted to a single stranded form and immobilized onto a carrier (e.g., nitrocellulose paper). The analyte nucleic acid may alternatively be electrophoresed into a gel matrix. The immobilized analyte may then be hybridized (i.e., specifically bound) by a complementary sequence of nucleic acid.

The foregoing specific binding assays may be performed in a wide variety of assay formats. These assay formats fall within two broad categories. In the first category, the assay utilizes a chemiluminescent conjugate which comprises the improved chemiluminescent moiety attached to a specific binding material. "Specific binding material" means herein any material which will bind specifically by an immunoreaction, protein binding reaction, nucleic acid hybridization reaction, and any other reaction in which the material reacts specifically with a restricted class of biological, biochemical or chemical species. In this category of assays, the chemiluminescent conjugate participates in a specific binding reaction and the presence of analyte in the sample is proportional to the formation of one or more specific binding reaction products containing the chemiluminescent conjugate. The assay is performed by allowing the requisite specific binding reactions to occur under suitable reaction conditions. The formation of specific binding reaction products containing the chemiluminescent conjugate is determined by measuring the chemiluminescence of such products containing the chemiluminescent conjugate or by measuring the chemiluminescence of unreacted or partially reacted chemiluminescent conjugate not contained in such products.

This first category of assay formats is illustrated by sandwich assays, competitive assays, surface antigen assays, sequential saturation assays, competitive displacement assays and quenching assays.

In a sandwich format, the specific binding material to which the chemiluminescent moiety is attached, is capable of specifically binding with the analyte. The assay further utilizes a reactant which is capable of specifically binding with the analyte to form a reactant-analyte-chemiluminescent conjugate complex. The reactant may be attached to a solid phase, including without limitation, dip sticks, beads, tubes, paper or polymer sheets. In such cases, the presence of analyte in a sample will be proportional to the chemiluminescence of the solid phase after the specific binding reactions are completed. Such assay formats are discussed further in U.S. Pat. Nos. 4,652,533, 4,383,031, 4,380,580 and 4,226,993, which are incorporated herein by reference.

In a competitive format, the assay utilizes a reactant which is capable of specifically binding with the analyte to form an analyte-reactant complex and with the specific binding material, to which the chemiluminescent moiety is attached, to form a chemiluminescent conjugate-reactant complex. The reactant may be attached to a solid phase, or alternatively reaction products containing the reactant may be precipitated by use of a second antibody or by other known means. In this competitive format, the presence of analyte is "proportional," i.e., inversely proportional, to the chemiluminescence of the solid phase or precipitate. A further discussion of this assay format may be found in the immediately above mentioned U.S. patents.

In another assay format, the analyte may occur on or be bound to a larger biological, biochemical or chemical species. This type of format is illustrated by a surface antigen assay. In this format, the specific binding material is capable of specifically binding with the analyte and the presence of analyte is proportional to the analyte-chemiluminescent conjugate complex formed as a reaction product. This is illustrated by attaching the chemiluminescent moiety to an antibody which is specific to a surface antigen on a cell. The presence of the cell surface antigen will be indicated by the chemiluminescence of the cells after the completion of the reaction. The cells themselves may be used in conjunction with a filtration system to separate the analyte-chemiluminescent conjugate complex which is formed on the surface of the cell from unreacted chemiluminescent conjugate. This is discussed further in U.S. Pat. No. 4,652,533.

The improved chemiluminescent moiety may be used in additional assay formats known in the art including without limitation sequential saturation and competitive displacement, both of which utilize a chemiluminescent conjugate where both (1) the specific binding material, to which the moiety is attached, and (2) the analyte specifically bind with a reactant. In the case of sequential saturation, the analyte is reacted with the reactant first, followed by a reaction of the chemiluminescent conjugate with remaining unreacted reactant. In the case of competitive displacement, the chemiluminescent conjugate competitively displaces analyte which has already bound to the reactant.

In a quenching format, the assay utilizes a reactant which is capable of specifically binding with the analyte to form an analyte-reactant complex and with the specific binding material, to which the chemiluminescent moiety is attached, to form a chemiluminescent conjugate-reactant complex. A quenching moiety is attached to the reactant. When brought into close proximity to the chemiluminescent moiety, the quenching moiety reduces or quenches the chemiluminescence of the chemiluminescent moiety. In this quenching format, the presence of analyte is proportional to the chemiluminescence of the chemiluminescent moiety. A further discussion of this format may be found in U.S. Pat. Nos. 4,220,450 and 4,277,437, which are incorporated herein by reference.

In consideration of the above discussed assay formats, and in the formats to be discussed below, the order in which assay reagents are added and reacted may vary widely as is well known in the art. For example, in a sandwich assay, the reactant bound to a solid phase may be reacted with an analyte contained in a sample and after this reaction the solid phase containing complexed analyte may be separated from the remaining sample. After this separation step, the chemiluminescent conjugate may be reacted with the complex on the solid phase. Alternatively, the solid phase, sample and chemiluminescent conjugate may be added together simultaneously and reacted prior to separation. As a still further but less preferred alternative, the analyte in the sample and the chemiluminescent conjugate may be reacted prior to addition of the reactant on the solid phase. Similar variations in the mixing and reaction steps are possible for competitive assay formats as well as other formats known in the art. "Allowing under suitable conditions substantial formation" of specific binding reaction products shall herein include the many different variations on the order of addition and reaction of assay reagents.

In the second category of assay formats, the assay utilizes an unconjugated improved chemiluminescent compound. The presence of analyte in the sample is proportional to the formation of one or more specific binding reaction products which do not themselves contain the chemiluminescent moiety. Instead, the chemiluminescent compound chemiluminesces in proportion to the formation of such reaction products.

In one example of this second category of assays, the assay utilizes a reactant capable of binding with the analyte to form an analyte-reactant complex which causes the chemiluminescent compound to chemiluminesce. This is illustrated by a simple enzyme-substrate assay in which the analyte is the substrate glucose and the reactant is the enzyme glucose oxidase. Formation of the enzyme-substrate complex triggers the chemiluminescent compound. Such enzyme-substrate assay for glucose is disclosed in U.S. Pat. Nos. 3,964,870 and 4,427,770, both of which are incorporated herein by reference. This enzyme-substrate assay is a specific binding assay in the sense that the substrate specifically binds to the active site of the enzyme in much the same way that an antigen binds to an antibody. In this assay, the enzyme specifically binds with the substrate which results in the production of peroxide which, in turn, causes the chemiluminescent compound to chemiluminesce.

Also included in the second category of assays are those assays in which the formation of the reaction products promotes or inhibits chemiluminescence by the chemiluminescent compound in a less direct manner. In this assay, a first reactant, which is cross reactive with the analyte, is attached to an enzyme such as glucose oxidase close to its active site. A second reactant which is specific for both the analyte and the immunoreactive material is added to the sample and the altered enzyme in the presence of the substrate (i.e., glucose). When the second reactant binds to the first reactant located near the active site on the enzyme, the second reactant blocks the active site in a way that the substrate cannot bind to the enzyme at the active site or the binding of the substrate at the active site is significantly decreased. The second reactant blocking the enzyme in this manner inhibits the enzyme from producing peroxide which, in turn, would have triggered the chemiluminescent moiety. Analyte in the sample, however, will tie up the second reactant, thus preventing the second reactant from inhibiting the production of peroxide. The presence of analyte will be proportional to the chemiluminescence of the compound.

The assays contained in the above two categories of assay formats may be heterogeneous or homogeneous. In heterogeneous assays, the reaction products, whose formation is proportional to the presence of analyte in the sample, are separated from other products of the reaction. Separation can be achieved by any means, including without limitation, separation of a liquid phase from a solid phase by filtration, microfiltration, double antibody precipitation, centrifugation, size exclusion chromatography, removal of a solid phase (e.g., a dip stick) from a sample solution or electrophoresis. For example, in a sandwich assay the reactant-analyte-chemiluminescent conjugate complex is separated from unreacted chemiluminescent conjugate. In a surface antigen assay, the analyte-chemiluminescent conjugate complex is separated from unreacted chemiluminescent conjugate. In a competitive assay, the reactant-chemiluminescent conjugate complex is separated from unreacted chemiluminescent conjugate. In a sequential saturation assay and in a competitive displacement assay, the reactant-chemiluminescent conjugate complex is separated from unreacted chemiluminescent conjugate.

Alternatively, in homogeneous assays the reaction products are not separated. After the assay reagents have been allowed to react, the chemiluminescence may be measured from the whole assay mixture whether such mixture is in solution, on a solid phase or distributed between various membrane layers of a dip stick or other solid support. The glucose assay using glucose oxidase and a chemiluminescent moiety illustrates a simple homogeneous assay in which separation is unnecessary. The quenching assay illustrates a more complex homogeneous assay in which separation is unnecessary. It is contemplated that either category of assay formats may give rise to either heterogeneous or homogeneous formats.

Finally, "measuring the chemiluminescence" shall include, where relevant, the act of separating those specific binding reaction products, the formation of which are proportional to the presence of analyte in the sample, from other reaction products. It shall also include, where relevant, the acts of triggering the chemiluminescent moiety to chemiluminesce in the case of those assay formats in which the formation of the reaction products does not itself trigger the chemiluminescent moiety.

SYNTHESIS OF MOIETIES

The following examples show the synthesis of certain chemiluminescent moieties of the present invention. These chemiluminescent moieties are typically made in small quantities and the procedures employed for their manufacture do not reflect conventional large scale chemical manufacturing procedures. In these reactions, conventional reactions have been employed to produce the chemiluminescent labels of the invention. Purification procedures suitable for isolating product are conventional laboratory procedures, such as crystallization out of solvent solution by the addition of a nonsolvent, solvent extraction, and the like. In such cases, many different solvents and nonsolvents are suitable. yields are the amounts recovered as a percentage of reactants employed.

EXAMPLE 1

The compound (2,6-dimethyl-4-trimethylammonio)-phenyl-N-methyl-acridinium-9-carboxylate difluorosulfonate has the following formula:

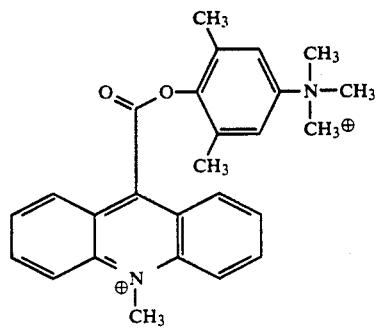

This compound, (2,6-dimethyl-4-trimethylammonio)-phenyl-N-methyl-acridinium-9-carboxylate difluorosulfonate, was synthesized according to the following scheme:

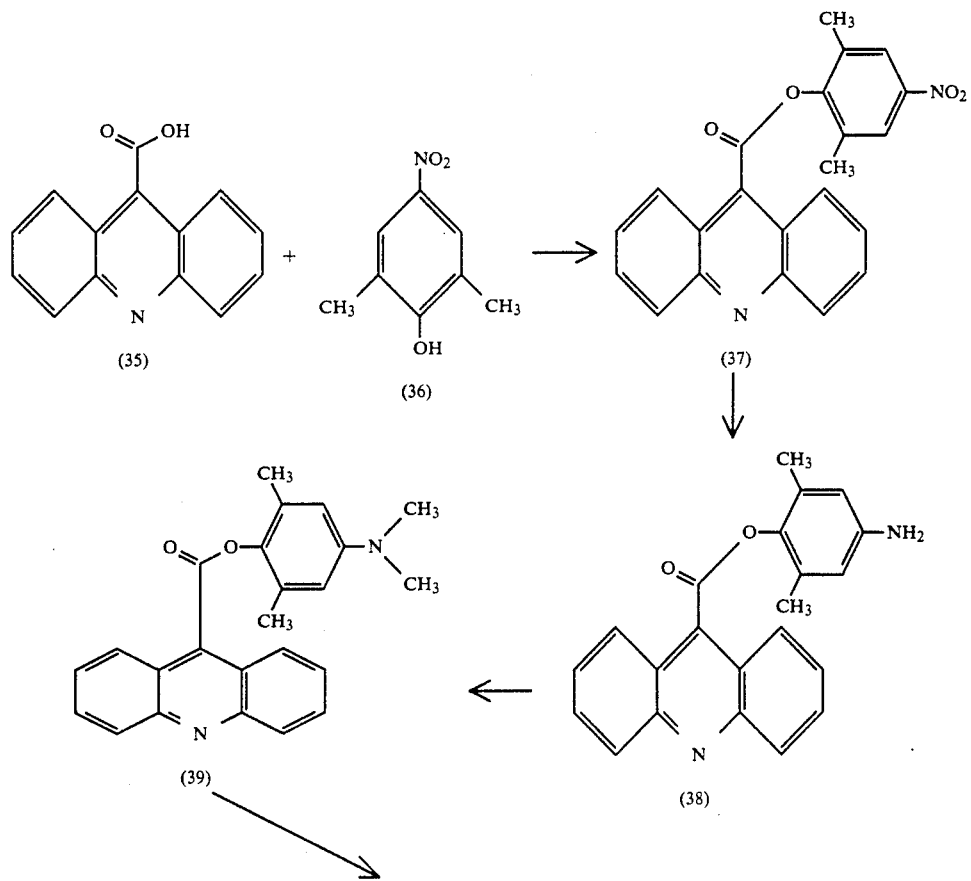

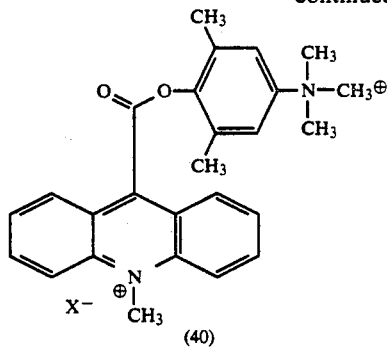

(40)

In the reaction scheme, (2,6-dimethyl-4-trimethylammonio)-phenyl-N-methyl-acridinium-9-carboxylate (40) was obtained by esterification of acridine-9-carboxylic acid (35) with 2,6-dimethyl-4-nitrophenol (36). The product (37) was reduced to the (2,6-dimethyl-4-amino)phenyl-acridine-9-carboxylate (38) with zinc. Two methyl groups were introduced on the amino group by treatment with methyl iodide. Quaternization and acridinium formation was then accomplished using methyl fluorosulfate. These reactions are described in further detail in the following.

Acridine-9-carboxylic acid (35) (3.05 g, 0.014 moles) in a 250 ml round bottom flask was mixed with thionyl chloride (65 ml) and the mixture was refluxed for 2 hours with stirring. The excess thionyl chloride was removed in a rotary evaporator. The residue was treated with benzene (75 ml) and the solvent was removed in vacuo to remove traces of thionyl chloride. The residue of acridine-9-carbonyl chloride was mixed with pyridine (65 ml) and 2,6-dimethyl-4-nitrophenol (36) (2.25 g, 0.014 moles) was added. The mixture was warmed using a water bath (about 60° C.) to dissolve all the solids. After 15 hours of stirring at room temperature the mixture was poured into 1 liter of water. The suspension was acidified with concentrated hydrochloric acid to pH 2.0. The solid product was filtered, washed with water and dissolved in chloroform. Drying (anhydrous sodium sulfate) and evaporation of chloroform gave the crude ester.

The crude ester was chromatographed on a silica gel column using CHCl$_3$/EtOAc 98:2 as solvent. The fractions with R$_f$ value of 0.6 on TLC with the same solvent were pooled and evaporation of the solvents gave pure (2,6-dimethyl-4-nitro)phenyl-acridine-9-carboxylate (37) (yield=30%).

The (2,6-dimethyl-4-nitro)phenyl ester (37) (1.16 g, 3.1 mmole) was dissolved in acetic acid (50 ml) by warming in an oil bath at about 65° C. Stannous chloride (1.5 g) was dissolved in concentrated hydrochloric acid (10 ml) and was added to the ester solution. The mixture was stirred for 45 minutes and was then poured into water (750 ml). Extraction with chloroform (3×200 ml) removed unreacted (2,6-dimethyl-4-nitro)phenyl ester. The aqueous layer was made basic with sodium bicarbonate and was extracted with chloroform (4×200 ml). Drying and evaporation of the chloroform gave (2,6-dimethyl-4-amino)phenyl-acridine-9-carboxylate (38) (yield=25%).

The amino ester (38) (64 mg, 0.18 mmole) was dissolved in nitromethane (5 ml). Methyl iodide (1 ml) and pyridine (0.1 ml) were added. The mixture was stirred at room temperature for 15 hours. Methanol (2 ml) was added and the mixture was then stirred for an additional 2 hours. The solvents were evaporated and the residue was treated with water (10 ml) and was then extracted with chloroform (4×20 ml) after the solution was made basic. Drying and evaporation of the chloroform gave (2,6-dimethyl-4-dimethylamino)phenyl-acridine-9-carboxylate (39) (yield=50%).

The dimethylamino ester (39) (154 mg. 0.41 mmole) was dissolved in methylene chloride (2 ml). Methyl fluorosupfate (265 1, 3.28 mmole) was added and the mixture was stirred at room temperature for 15 hours. Amhydrous ether (15 ml) was added and the precipitated solids were filtered and washed with ether. Drying gave (2,6-dimethyl-4-trimethylammonio)phenyl-N-methyl-acridinium-9-carboxylate (40) (yield=50%). MS: FAB, thioglycerol matrix, m/e 400 (M+).

EXAMPLE 2

The following procedure for attaching to protein is generally applicable to chemiluminescent labels of the present invention.

Mouse IgG (Sigma, 1 mg) is dissolved in 0.9 ml phosphate buffer (100 mM, pH 8.0, 150 mM). If desired, higher pH may be employed, such as a pH as high as 9.5. The solution is then divided into three equal portions of 0.33 mg/0.3 ml (0.0022 μmoles). About 0.3 mg of a moiety of the present invention is dissolved in about 0.4 ml DMF so as to obtain 0.022 μmoles of moiety in 15 μl DMF.

0.022 μmoles of the compound of the present invention is mixed with 0.0022 μmoles of IgG in a plastic microcentrifuge tube. After 15 minutes, an additional 0.022 μmoles of compound is added to the microcentrifuge tube (compound to protein molar ratio was 20:1). After an additional 15 minutes, excess amounts of the compound of the present invention are quenched with lysine HCl solution (10 μl in 100 mM p$_t$buffer, pH 8.0) for 15 minutes.

Alternatively, aliquots of 0.0055 μmoles of the compound of the present invention is used instead of 0.022 μmoles (compound to protein molar ratio was 5:1).

Biorad glass columns (1 cm×50 cm) (commercially available from Biorad, Chemical Division, Richmond, Calif.) are packed with previously swelled and deaerated Sephadex G-50-80 in phosphate buffer (100 mM, pH 6.3, 150 mM NaCl, 0.001% TMS) to a bed volume of 45 ml. The reaction solution is run through the columns at a flow rate of 0.3–0.4 ml/min. 0.5 ml fractions are collected. Labelled protein fractions are detected by diluting 20 μl from each fraction to 1 ml and determining the chemiluminescence produced with 30 μl of the diluted solution. Labelled fractions are then pooled.

The pooled conjugate fractions are dialyzed to improve the purity of immunoreactive conjugate. The pooled fractions are dialyzed against 500 ml pH 6.3 phosphate buffer (100 mM, pH 6.3, 150 mM NaCl, 0.001% TMS) over a period of 24 hours with three buffer changes.

From the foregoing, it will be obvious to those skilled in the art that various modifications in the above-described compositions and methods can be made without departing from the spirit and scope of the invention. Accordingly, the invention may be embodied in other specific forms without departing from the spirit or essential characteristics thereof. Present embodiments, therefore, are to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A novel chemiluminescent aryl ester or thiolester of a carboxylic acid substituted heterocyclic ring that is susceptible to chemical attack to dissociate the heterocyclic ring to a transient compound, wherein the heterocyclic ring is ring carbon-bonded to the carbonyl of the ester or thiolester moiety and possesses a heteroatom in an oxidation state that allows chemiluminescence by dissociating a compound at the carbon bonded to the carbonyl that decays to produce chemiluminescence, the aryl is a ring or ring system that is ring carbon-bonded to the oxygen, quaternary ammonium or sulfur of the ester or thiolester, as the case may be, and contains at least three substituents thereon directly bonded thereto acting in concert to sterically and electronically hinder hydrolysis of the ester or thiolester linkage, one of which is quaternary ammonium in a meta or para position.

2. A hydrolytically stable heterocyclic composition capable of chemiluminescent properties when labeled to a specific binding material by chemically-induced dissociation, comprising
   (a) an aryl ring,
   (b) a sterically-hindered ester or thiolester linkage moiety with enhanced hydrolytic stability, and
   (c) a heterocyclic organic ring moiety, in which
      (1) the carbonyl carbon of (b) is covalently bonded to a carbon atom (x) of (c) and the remaining free valence of (b) is carbon bonded to an aromatic ring carbon atom (y) of (a),
      (2) (a) contains at least three substituent groups hindering hydrolysis of (b), two of which are electron donating and located on the ring carbon atoms adjacent to (y), the remainder comprise quaternary ammonium meta or para carbon bonded directly to (y), and
      (3) (c) contains
         (i) at least one ring carbon atom adjacent to said ring carbon atom (x), and
         (ii) a ring member heteroatom in an oxidation state that provides such chemiluminescence properties.

3. A hydrolytically stable conjugate possessing chemiluminescent properties by chemical dissociation, comprising a chemiluminescent label bonded to a specific binding material that contains
   (a) an aryl ring,
   (b) a sterically-hindered ester or thiolester linkage moiety with enhanced hydrolytic stability, and
   (c) a heterocyclic organic ring moiety, in which
      (1) the carbonyl carbon of (b) is covalently bonded to a carbon atom (x) of (c) and the remaining free valence of (b) is carbon bonded to an aromatic ring carbon atom (y) of (a),
      (2) (a) contains at least three substituent groups hindering hydrolysis of (b), two of which are electron donating and located on the ring carbon atoms adjacent to (y), the remainder comprises quaternary ammonium meta or para carbon bonded directly to (y), and
      (3) (c) contains
         (i) at least one ring carbon atom adjacent to said ring carbon atom (x), and
         (ii) a ring member heteroatom that is in an oxidation state whereby reaction of molecular oxygen or a peroxide with said composition forms an intermediate which decays to produce chemiluminescence.

4. The chemiluminescent labeling composition of claim 1 conjugated with a specific binding material.

5. A chemiluminescent assay comprising the conjugate of claim 3.

6. A chemiluminescent assay kit comprising the conjugate of claim

7. A hydrolytically stable heterocyclic composition capable of chemiluminescent properties when labeled to a specific binding material, by reaction with peroxide or molecular oxygen, comprising
   (a) an aryl ring,
   (b) a sterically-hindered ester or thiolester linkage moiety with enhanced hydrolytic stability, and
   (c) a heterocyclic organic ring moiety, in which
      (1) the carbonyl carbon of (b) is covalently bonded to a carbon atom (x) of (c) and the remaining free valence of (b) is carbon bonded to an aromatic ring carbon atom (y) of (a),
      (2) (a) contains at least three substituent groups hindering hydrolysis of (b), two of which are electron donating and located on the ring carbon atoms adjacent to (y), the remainder contains quaternary ammonium meta or para carbon bonded directly to (y), and
      (3) (c) contains
         (i) at least one ring carbon atom adjacent to said ring carbon atom (x), and
         (ii) a ring member heteroatom in an oxidation state that provides such chemiluminescence properties.

8. A hydrolytically stable conjugate possessing chemiluminescent properties by reaction of molecular oxygen or a peroxide therewith, comprising a chemiluminescent label bonded to a specific binding material that contains
   (a) an aryl ring,
   (b) a sterically-hindered ester or thiolester linkage moiety with enhanced hydrolytic stability, and
   (c) a heterocyclic organic ring moiety, in which
      (1) the carbonyl carbon of (b) is covalently bonded to a carbon atom (x) of (c) and the remaining free valence of (b) is carbon bonded to an aromatic ring carbon atom (y) of (a),
      2) (a) contains at least three substituent groups hindering hydrolysis of (b), two of which are electron donating and located on the ring carbon atoms adjacent to (y), the remainder comprise quaternary ammonium meta or para to (y), and
      (3) (c) contains (i) at least one ring carbon atom adjacent to said ring carbon atom (x), and (ii) a ring member heteroatom that is in an oxidation state whereby reaction of molecular oxygen or a peroxide with said composition forms an intermediate which decays to produce chemiluminescence.

9. An assay for the presence of an analyte in a sample comprising contacting an analyte with the chemiluminescent-labeled specific binding material of claim 8, inducing chemiluminescence by decay of an intermediate formable in the presence of peroxide or molecular oxygen, and measuring chemiluminescence therefrom to assay the analyte.

10. A specific binding assay kit comprising a vial containing a conjugate possessing chemiluminescent properties by reaction of molecular oxygen or a peroxide therewith and containing the chemiluminescent label bonded to a specific binding material of claim 8.

11. The chemiluminescent aryl ester or thiolester composition of claim 1 wherein the composition is of the formula:

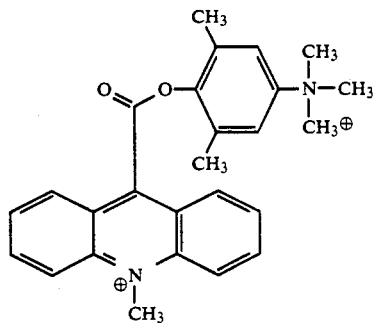

12. The novel chemiluminescent compound of claim 1 wherein the heterocyclic ring is from the group consisting of acridinium, benz[a]acridinium, benz[b]acridinium, benz[c]acridinium, a 1,2,4-triazole cation, an isooxazole cation, an isothioazole cation, a 1,2-azole cation, an imidazole cation, a benzimidazole cation, quinolinium, isoquinolinium, quinolizinium, a cyclic substituted quinolinium, pyridinium, pyrimidininium, pyridazinium, pyrazininium, phenanthridinium, and quinoxalinium.

13. The novel chemiluminescent compound claim 2 wherein the heterocyclic ring is from the group consisting of acridinium, benz[a]acridinium, benz[b]acridinium, benz[c]acridinium, a 1,2,4-triazole cation, an isooxazole cation, an isothioazole cation, a 1,2-azole cation, an imidazole cation, a benzimidazole cation, quinolinium, isoquinolinium, quinolizinium, a cyclic substituted quinolinium, pyridinium, pyrimidininium, pyridazinium, pyrazininium, phenanthridinium, and quinoxalinium.

14. The hydrolytically stable heterocyclic composition of claim 3 wherein the heterocyclic ring is from the group consisting of acridinium, benz[a]acridinium, benz[b]acridinium, benz[c]acridinium, a 1,2,4-triazole cation, an isooxazole cation, an isothioazole cation, a 1,2-azole cation, an imidazole cation, a benzimidazole cation, quinolinium, isoquinolinium, quinolizinium, a cyclic substituted quinolinium, pyridinium, pyrimidininium, pyridazinium, pyrazininium, phenanthridinium, and quinoxalinium.

15. The hydrolytically stable heterocyclic composition of claim 7 wherein the heterocyclic ring is from the group consisting of acridinium, benz[a]acridinium, benz[b]acridinium, benz[c]acridinium, a 1,2,4-triazole cation, an isooxazole cation, an isothioazole cation, a 1,2-azole cation, an imidazole cation, a benzimidazole cation, quinolinium, isoquinolinium, quinolizinium, a cyclic substituted quinolinium, pyridinium, pyrimidininium, pyridazinium, pyrazininium, phenanthridinium, and quinoxalinium.

16. The novel chemiluminescent compound of claim 1 wherein it has the formula:

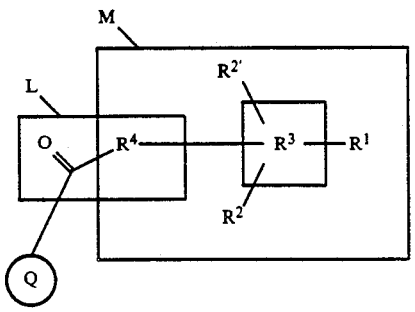

in which L contains the ester, thiolester or amide linkage which is carbon-bonded between two substituted rings or ring systems Q and $R^3$; $R^4$ is —O—, —S— or —NT—; T is a stable quaternary ammoniumgen bonded group; M is a leaving group comprising a portion of L and moiety $R^3$ with its associated $R^1$, $R^2$ and $R^{2'}$ bonded thereto; $R^3$ is an aryl group covalently bonded to $R^4$; $R^1$ is quaternary ammonium directly bonded meta and/or para to the carbon of $R^3$ bonded to $R^4$; $R^2$ and $R^{2'}$ are bulky electron donating groups bonded ortho to the bond of $R^4$ to $R^3$; M is a leaving group which possesses a $pK_a$ of about $\leq 11$; Q is a heterocyclic ring or ring system to which the ester, thiolester or amide linkage L is attached at a carbon atom within the heterocyclic ring or ring system, which carbon atom (1) is either $sp^2$ or $sp^3$ hybridized, and (2) is susceptible to attack by peroxide or molecular oxygen to form the intermediate that decays to produce chemiluminescence, the oxidation state of the heteroatom within the heterocyclic ring or ring system determining whether the carbon atom is susceptible to such attack and if the carbon to which the linkage is attached is $sp^2$ hybridized, the heteroatom is in a positive oxidation state, and if the carbon to which the linkage is attached is $sp^3$ hybridized, the heteroatom is in a neutral oxidation state, and where the heteroatom is quaternary ammoniumgen, the quaternary ammoniumgen is substituted with an alkyl group or a reactive functionalized alkyl group, an aryl group or a reactive functionalized aryl group, —O— where the quaternary ammoniumgen is in a positive oxidation state or —OH where the quaternary ammoniumgen is in a neutral oxidation state, such that the carbon atom is susceptible to attack by peroxide or molecular oxygen to produce a chemiluminescent intermediate.

17. The novel chemiluminescent compound of claim 16 wherein the heterocyclic rings or ring systems that contain the heteroatom in a positive oxidation state are from the group consisting of acridinium, benz[a]acridinium, benz[b]acridinium, benz[c]acridinium, a 1,2,4-triazole cation, an isooxazole cation, an isothioazole cation, a 1,2-azole cation, an imidazole cation, a benzimidazole cation, quinolinium, isoquinolinium, quinolizinium, a cyclic substituted quinolinium, pyridinium, pyrimidininium, pyridazinium, pyrazininium, phenanthridinium, and quinoxalinium and the heterocyclic rings or ring systems in which the heteroatom is in a neutral oxidation state are the reduced forms of acridinium, benz[a]acridinium, benz[b]acridinium, benz[c]acridinium, a 1,2,4-triazole cation, an isooxazole cation, an isothioazole cation, a 1,2-azole cation, an imidazole cation, a benzimidazole cation, quinolinium, isoquinolinium, quinolizinium, a cyclic substituted quinolinium, pyridinium, pyrimidininium, pyridazinium, pyrazininium, phenanthridinium, and quinoxalinium.

18. The novel chemiluminescent compound of claim 17 wherein $R^3$ includes at least one substituted six-member ring of the formula

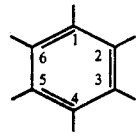

in which the substituents comprise at least one $R^1$ at ring carbons 3, 4 and 5, and $R^2$ and $R^{2'}$ at ring carbons 2 and 6; $R^4$ is directly attached through a covalent bond to the six-member ring at ring carbon 1; $R^3$ is one of phenyl, naphthyl and anthracyl and in those cases where napthyl or anthracyl rings are employed, one of the rings constitutes $R^3$ and the other ring or rings in combination with it are formed via ring carbons thereof other than carbon 1.

* * * * *

UNITED STATES PATENT AND TRADEMARK OFFICE
CERTIFICATE OF CORRECTION

PATENT NO. : 5,281,712

DATED : Jan. 25, 1994

INVENTOR(S) : Frank McCapra, et al.

It is certified that error appears in the above-indentified patent and that said Letters Patent is hereby corrected as shown below:

At column 24, line 25: after "claim" insert ---4.---

Signed and Sealed this

Eleventh Day of October, 1994

Attest:

BRUCE LEHMAN

Attesting Officer     Commissioner of Patents and Trademarks